United States Patent
Heinrich et al.

(10) Patent No.: US 10,121,062 B2
(45) Date of Patent: Nov. 6, 2018

(54) DEVICE, SYSTEM AND METHOD FOR AUTOMATED DETECTION OF ORIENTATION AND/OR LOCATION OF A PERSON

(71) Applicant: KONINKLIJKE PHILIPS N.V., Eindhoven (NL)

(72) Inventors: Adrienne Heinrich, Eindhoven (NL); Yingrong Xie, Eindhoven (NL); Esther Marjan Van Der Heide, Eindhoven (NL); Thomas Falck, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 144 days.

(21) Appl. No.: 14/930,212

(22) Filed: Nov. 2, 2015

(65) Prior Publication Data
US 2016/0125620 A1    May 5, 2016

(30) Foreign Application Priority Data
Nov. 3, 2014  (EP) .................................. 14191395

(51) Int. Cl.
*G06K 9/00* (2006.01)
*G06K 9/62* (2006.01)
(Continued)

(52) U.S. Cl.
CPC .......... *G06K 9/00335* (2013.01); *A61B 5/002* (2013.01); *A61B 5/0077* (2013.01);
(Continued)

(58) Field of Classification Search
None
See application file for complete search history.

(56) References Cited

U.S. PATENT DOCUMENTS 5,930,379 A     7/1999  Rehg
6,049,281 A *   4/2000  Osterweil ............ A61B 5/1128
                                                340/573.1
(Continued)

FOREIGN PATENT DOCUMENTS

NZ         534482 A      5/2007
WO     2012164453 A1    12/2012
(Continued)

OTHER PUBLICATIONS

Aggarwal, J.K. et al "Human Motion: Modeling and Recognition of Actions and Interactions", Proceedings of the 2nd International Symposium on 3D Data Processing, Visualization, and Transmission 2004.
(Continued)

*Primary Examiner* — Matthew Bella
*Assistant Examiner* — Jose M Torres

(57) ABSTRACT

A device, system and method automatically detects orientation and/or location of a person. To increase the robustness and accuracy, the device includes an image data interface (20) for obtaining image data of a person (110), which image data includes a sequence of image frames over time, a motion detector (21) for detecting motion within said image data, a motion intensity detector (22) for identifying motion hotspots representing image areas showing frequently occurring motion, and a person detector (23) for detecting the orientation and/or location of at least part of the person (110) based on the identified motion hotspots.

16 Claims, 9 Drawing Sheets

(51) Int. Cl.
*A61B 5/00* (2006.01)
*A61B 5/11* (2006.01)
*G06T 7/73* (2017.01)
*G06T 7/13* (2017.01)
*G06T 7/215* (2017.01)
*G06T 7/246* (2017.01)

(52) U.S. Cl.
CPC ........... *A61B 5/1113* (2013.01); *A61B 5/1128* (2013.01); *G06K 9/628* (2013.01); *G06K 9/6218* (2013.01); *G06T 7/13* (2017.01); *G06T 7/215* (2017.01); *G06T 7/246* (2017.01); *G06T 7/73* (2017.01); *A61B 5/0037* (2013.01); *A61B 2576/00* (2013.01); *G06T 2207/10016* (2013.01); *G06T 2207/30196* (2013.01)

(56) References Cited

U.S. PATENT DOCUMENTS

| | | | | |
|---|---|---|---|---|
| 7,477,285 | B1* | 1/2009 | Johnson | G06F 19/327 348/143 |
| 8,743,200 | B2* | 6/2014 | Anderson | G08B 21/02 348/143 |
| 9,041,810 | B2* | 5/2015 | Ecker | G06K 9/00348 348/152 |
| 9,295,390 | B2* | 3/2016 | Receveur | A61B 5/002 |
| 9,396,543 | B2* | 7/2016 | Uetsuji | G06T 7/0051 |
| 9,579,047 | B2* | 2/2017 | Clark | A61B 5/002 |
| 2003/0058111 | A1* | 3/2003 | Lee | G06K 9/00342 340/573.1 |
| 2009/0278934 | A1* | 11/2009 | Ecker | G06K 9/00348 348/152 |
| 2012/0026308 | A1* | 2/2012 | Johnson | G06K 9/00369 348/77 |
| 2012/0075464 | A1* | 3/2012 | Derenne | A61B 5/0013 348/135 |
| 2012/0154582 | A1* | 6/2012 | Johnson | G06F 19/321 348/143 |
| 2013/0215248 | A1* | 8/2013 | Ishii | A61B 5/1113 348/77 |
| 2013/0245389 | A1* | 9/2013 | Schultz | A61B 5/0002 600/301 |

FOREIGN PATENT DOCUMENTS

| | | |
|---|---|---|
| WO | 2013050912 A1 | 4/2013 |
| WO | 2015011591 A1 | 1/2015 |

OTHER PUBLICATIONS

Buchsbaum, Daphna et al "Segmenting and Recognizing Human Action using Low-Level Video Features", Proc. of the 33rd Annual Conference of the Cognitive Science Society, 2011.

Gelgon, Marc et al "A Region-Level Graph Labeling Approach to Motion-Based Segmentation", Dec. 1996.

Hauptmann, Alexander G. et al "Automatic Analysis of Nursing Home Observations", Pervasive Computing 2004.

Heinrich, A. et al "Optimization of Hierarchical 3DRS Motion Estimators for Picture Rate Conversion", IEEE. Journal Signal Processing, vol. 5, No. 2, 2010 Abstract Only.

Kakadiaris, Ioannis et al "Active Motion-Based Segmentation of Human Body Outlines "Penn Libraries, Technical Reports, Nov. 1994.

Shyamsunder, R. et al "Compression of Patient Monitoring Video Using Motion Segmentation Techinique", Journal Medical System vol. 31, 2007.

Tekalp, A. Murat "Video Segmentation" Handbook of Image and Video Processing, 2014.

* cited by examiner

DEVICE, SYSTEM AND METHOD FOR AUTOMATED DETECTION OF ORIENTATION AND/OR LOCATION OF A PERSON

FIELD OF THE INVENTION

The present invention relates to a device, system and method for automated detection of orientation and/or location of a person.

BACKGROUND OF THE INVENTION

In the area of patient monitoring, movement monitoring can give information about a patient's clinical condition. Dangerous situations could be communicated to the medical staff, such as getting/falling out of bed, pulling of medical equipment (for example the endotracheal tube or feeding tube) or disease specific movements such as grabbing in the air, repetitive movement of legs in the case of delirium, epileptic seizures, etc.

Change in motoric behavior is one of the core features of delirium. Besides changes in overall activity levels (e.g. decreased activity levels for the hypoactive subtype) delirious patients also show unusual movements such as grabbing in the air, picking of the skin or bed sheets, and restless movements of the legs. Movement analysis and movement classification can be of great importance for delirium detection.

In previous studies wrist-worn accelerometer techniques were used to analyze the change in activity levels due to delirium. The on-body wrist sensor may be disturbing or even confusing for the patient. More importantly, it does not capture movements performed by other body parts nor does it provide the possibility for a higher-level interpretation of the movements, such as 'pinching the skin', 'grabbing in the air'. Continuous and automatic video monitoring is believed to offer the opportunity to go beyond these limitations.

In order to recognize/classify patient movements, features of natural and unusual movements are extracted from the images/videos and fed to a classifier. Feature extraction for patient monitoring is commonly performed globally, on the entire body. Yet, movement classification profits from body part information as particular movements are often performed by specific body parts (e.g., moving head continuously from left to right is unusual whereas a repetitive hand movement while eating is not). Thus, the classification outcome improves greatly when features can be extracted per body part.

When patient monitoring with a video camera is performed with the purpose to monitor the vital signs, the chest area (for monitoring breathing) or face area (for monitoring heart rate) is important information.

Thus, for both movement analysis and vital signs monitoring, information on patient region of interest (ROI) and on the location of the main body parts in the image are crucial. This does not only hold for patients, e.g. in a hospital, but generally for all persons, like elderly persons in a nursing home or at their own home, who shall be monitored, or for a child or newborn in an incubator.

In many cases, in the hospital a patient's motoric behavior is mostly only observed when the medical staff visits the patient or sometimes by using checklists. Detection of change in motoric behavior between the past and current visit is often difficult to notice by the medical staff. This type of inspection introduces non-negligible lag in the detection of critical problems, such as the onset of diseases revealed by change in motoric behavior or critical situations induced by the patients' movements.

Other sensors than the video camera are suggested in literature to monitor the patients motoric behavior, however they are often specialized to detect a particular incident (e.g., patient falling out of bed). Video data is rich in information e.g., the possibility to detect patient's face, hands, analyze movements, analyze interaction with objects or recognize general behavior. Therefore, the video sensor offers the opportunity to automatically analyze and recognize different types of movements performed by the patient.

Automatic video-based monitoring of patients is a relatively new topic and the developed tools are at their infancy. The video analysis methods have to cope with the dynamic aspects of the hospital. These can be scene variations such as the changes in the bed angle and bed backrest tilt, persons or objects like the TV screen occluding parts of the patient, different patient lying positions in bed and a blanket covering body parts of the patient and the entrance and the disappearance of the medical personnel and visitors. These challenges make it difficult to include typical body segmentation methods and identification of body parts for patient monitoring. The presence of the blanket makes it difficult to fit a human model on the lying patient; the scene variations limit current video analysis methods for body part segmentation (such as edge/gradient analysis, luminance value analysis, and object detection).

SHYAMSUNDER R ET AL: 11 Compression of Patient Monitoring Video Using Motion Segmentation Technique, JOURNAL OF MEDICAL SYSTEMS. KLUWER ACADEMIC PUBLISHERS-PLENUM PUBLISHERS. NE. vol. 31. no. 2. 21 Mar. 2007 discloses a motion segmentation technique for the separation of stationary and moving portions in a video using a binary mask.

NZ 534482 A discloses methods and systems for objectively determining the level of agitation in a patient. The method involves automated monitoring of physical movement of a defined region of interest of the patient's body, and/or monitoring expert systems that delineate other clinical events from agitation (e.g. atrial fibrillation from large spikes in heart rate due to agitation). Signal processing is performed on physiological signals associated with the monitoring, and changes in the processed signals allow the level of patient agitation to be quantified.

WO 2012/164453 A1 discloses methods and apparatus for monitoring movement and breathing of two or more subjects occupying common bedding. The method comprises the steps of imaging the bedding by an optical sensor; performing a motion estimation by producing motion vectors indicating the local displacement of corresponding image blocks between consecutive images, or images that are several frames apart, received from said optical sensor; calculating motion clusters by measuring spatial and temporal correlations of the motion vectors; and segmenting the calculated motion clusters by assignment of each motion cluster to a corresponding subject, wherein the assignment of the motion clusters to the corresponding subject is based on the spatial and/or temporal similarity of the motion clusters among each other and on previous segmentation results.

SUMMARY OF THE INVENTION

It is an object of the present invention to provide a device, system and method that enable a robust automated detection of orientation and/or location of a person.

In a first aspect of the present invention a device for automated detection of orientation and/or location of a person is presented comprising an image data interface for obtaining image data of a person, said image data comprising a sequence of image frames over time.

a motion detector for detecting motion within said image data.

a motion intensity detector for identifying motion hotspots representing image areas showing frequently occurring motion, a person detector for detecting the orientation and/or location of at least part of the person based on the identified motion hotspots.

In a further aspect of the present invention a corresponding method for automated detection of orientation and/or location of a person is presented.

In still a further aspect of the present invention a system for automated detection of orientation and/or location of a person is presented comprising an imaging unit for acquiring image data of a person, said image data comprising a sequence of image frames over time, a device as disclosed herein for automated detection of orientation and/or location of at least part of the person based on the acquired image data, and an output interface for issuing information related to the detected orientation and/or location of at least part of the person.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

The present invention is based on the idea identify motion hotspots within said image data, i.e. within a series of image frames and to use such motion hotspots for determining the orientation and/or location of at least part of the person. Hereby, a motion hotspot shall be understood as an image area which shows frequently occurring motion, i.e. an image area in which a lot of motion has been detected. For instance, if the person is lying in bed, and continuously shakes his head, the head area would be detected as such a motion hotspot. Such motion hotspots generally result from taking a plurality of image frames (up to thousands of image frames) into account.

By use of such motion hotspots the region of interest (ROI) of the person, such as a rough body outline, or at least one or more characteristic body parts of the person, such as the head, arms, legs, can be rather accurately determined, depending on the kind of scenario, the application, and the particular circumstances of the monitoring (e.g. if other persons are in the field of view and thus shown in the image data, how much the person moves, etc.).

The invention is preferably applicable if the person is in a resting position, such as lying in bed or on a couch, sitting on a chair, standing still, etc. However, the invention can also be applied in other situations, as long as the person is present in the same image area over time. The person can move, stand, sit, or lie as long as he stays more or less in the same area. Then motion hotspots in this area correspond to the patient movements and the ROI can be computed.

The proposed video-based patient monitoring system is relatively inexpensive and unobtrusive. It can continuously and automatically monitor not only the patient's whole body activity, but also the movements from a particular body part. With advanced computer vision technology, specific motions can be identified.

In preferred embodiments, as explained below, one or more of left, right, top, bottom boundaries of the person can be determined. Further, an accumulation of motion images identifying areas with frequently occurring motion can be used for the detection of motion hotspots. This accumulation can be based on motion detection or motion estimation. Still further, a computation of the head location may be obtained based on the location of frequent interaction between regions outside the person ROI and the person ROI itself. The proposed device, system and method are robust, even in view of potential compression artifacts caused by a potential compression of the image data before processing as proposed, and may even be able to distinguish between nurse movement and patient movement.

In another preferred embodiment said motion detector is configured to determine motion images representing motion detected within said image data from one image frame to another image frame and wherein said motion intensity detector is configured to identify motion hotspots by accumulating said motion images. A motion image may hereby e.g. be a motion vector field image or an image with detected motion pixels, which can e.g. be obtained by a conventional motion estimation algorithm or other known methods for detecting motion in a time series of image frames of a scene. The obtained accumulation image(s) of such motion images may then directly show image areas having a high amount of motion and/or strong motion (which are considered as motion hotspots) as well as other image areas with less or no motion. This provides a practical and reliable way for determining motion hotspots.

Preferably, said motion intensity detector is configured to accumulate motion images, in particular motion images covering a predetermined time period, to obtain one or more accumulation images by summing up binary occurrences of motion pixels or motion vector information (e.g., vector length) within two or more motion images. The predetermined time period may generally be a time period within which movements of the person can be expected. When the person is more sedentary as in the ICU it may be a longer time frame than when the person is relatively active. Thus, the predetermined time period may only be a few minutes, but also one or several hours may be used as well.

In a preferred embodiment, said motion intensity detector is configured to identify image areas as motion hotspots, which have a size above a size threshold or the largest sizes within one or more accumulation images and which show motion above a motion threshold or the most intensive motions. Such thresholds may e.g. be set in advance, for instance based on earlier experiments with different scenarios and types of motion. Such thresholds are used to detect the most frequently occurring movement areas. It can be set in a fixed way or as a percentage of the maximum movement occurrences measured for one person (from several different time periods in order to exclude a bias to time periods where hardly any movement occurred). The threshold can also be empirically determined per use case.

In another embodiment said person detector is configured to identify the motion hotspot showing the most intensive motions over a predetermined time period as a first boundary, in particular an upper boundary, of a person in an image. The upper boundary may be the head area of the person, but not necessarily. In a preferred application, images are obtained from the person from the side, e.g. when the person is in a lying position such as in a patient bed in a hospital. In this application the upper boundary in the image corresponds to either the left or right side of the person since this is the upper boundary of the person in the image. Above the hotspot where there is less motion, the person is not assumed to be present. Motion would then be caused e.g. by a nurse moving in said area once in a while. In other applications the person may be in a vertical position or the images may be acquired from a different position. Thus, if the person has another orientation, the images may first be rotated before application of the proposed steps.

Advantageously, said person detector is configured to identify the motion hotspot located farthest away from the first boundary towards an edge of the image opposite the first boundary as a second boundary, in particular as the lower boundary, of the person in an image. This further helps to identify the area in which the person is arranged.

Even further, in an embodiment said person detector is configured to detect a third and/or fourth boundary, in particular a left and/or right boundary, of the person in an image, in particular by edge strength analysis in one or more accumulated images in a direction substantially parallel to the longitudinal axis of the person. This may be obtained by an embodiment in which said person detector is configured to cluster, preferably individually per image row, (strong) edges detected in several accumulated images and to identify the largest cluster of edges to the left and right, respectively, as the respective boundary. In a preferred embodiment a kind of edge strength analysis is performed on the motion images with the motion hotspots. So on passing through the image e.g. from the left to the right, there comes the time when a strong motion hotspot starts which belongs to the person. This indicates a first (e.g. the left) boundary because the edge is strong (which shall be understood by the explanation that it "exceeds k times the mean of the previous values").

There will also be some edges because a nurse may have moved in the image next to the bed, but they are not that strong. When this edge analysis is done not only for one image row but for all the rows between the upper and lower boundary, pixel coordinates with strong edge locations are returned. The resulting left boundary is then set to the pixel coordinate where the most pixel coordinates with strong edge locations were found.

In another preferred embodiment said person detector is configured to detect the presence, orientation and/or location of one or more additional persons or at least parts thereof based on the identified motion hotspots and to use the result of this detection in the detection of the orientation and/or location of at least part of the person. It is thus possible to distinguish e.g. between the patient on the one hand and a nurse, a doctor or a visitor on the other hand, for instance based on the amount, area, intensity, pattern, etc. of detected motion. Thus, said person detector may be configured to use the intensity, location, pattern and/or duration of motion of said one or more additional persons in the detection of the presence, orientation and/or location of one or more additional persons or at least parts thereof and/or in the orientation and/or location of at least part of the person.

Further, in an embodiment said person detector may be configured to identify the location of body parts of the person based on the detected first and/or second boundary and known or average body proportions of the person. The monitored person may even be classified into a particular class, wherein each class may be assigned typical (average) body proportions which are then used in the estimation of the person's location and/or orientation. This will further improve the accuracy of the estimation.

The proposed device may further comprise an analysis unit for analyzing movements of the person or one or more body parts of the person over time based on the detected orientation and/or location of at least part of the person as detected regularly, continuously or from time to time, and an evaluation unit for classifying the detected movements into natural and unusual movements, determining a disease severity score estimation and/or issuing an information signal in case the analyzed movements exceed predetermined criteria for issuing an information signal. As explained above, patients suffering from a certain disease show disease-typical movements, such as patients suffering from delirium, Parkinson, epilepsy, restless legs, etc. This embodiment can thus be used to detect such a disease, potentially even in an early stage, or to detect when the patient shows a disease-typical activity, which may need a particular care or monitoring. In particular, unusual movements related to diseases and/or disorders such as grabbing in the air in case of delirium or epileptic seizures, can be recognized and taken into account when assessing the patient's health condition. This movement identification can also provide additional benefits. For instance, if some special or dangerous movement is detected, such as pulling off medical equipment or getting out of bed without assistance, the system can send a warning message to medical staff.

In an embodiment a disease severity score is estimated based on various video analyses of patient's movements, which will support clinical staff to determine the clinical condition of the patient. It works in an automatic and continuous way, leading to a more effective video-based monitoring method.

For image acquisition of the image data of the person an imaging unit, such as a video camera (e.g. a web cam or a surveillance camera, which continuously, regularly or from time to time obtains image frames over time. For outputting the detected orientation and/or location of at least part of the monitored person an output interface, such as an interface for transmitting data to a server, computer, display, smartphone or some other entity is used, wherein the transmission may be made in wired or wireless manner, e.g. via LAN, Wi-Fi, UMTS, direct cabling or in any useful way.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
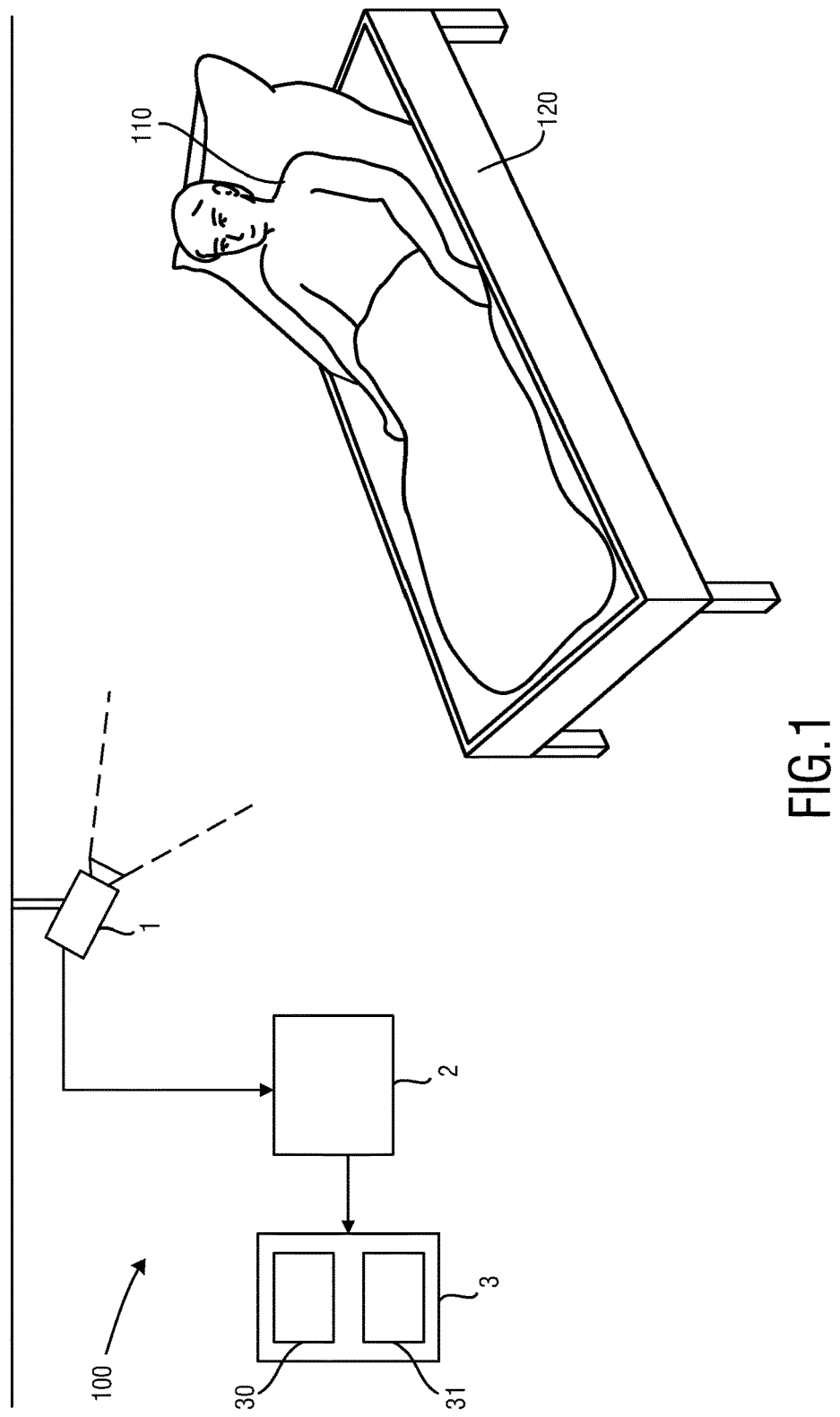
FIG. 1 shows a schematic diagram of the general layout of a system and a device according to the present invention.

FIG. 1 shows a schematic diagram of the general layout of a system 100 and a device 2 according to the present invention for automated detection of orientation and/or location of a person 110. The system 100 comprises an imaging unit 1 for acquiring image data of a person 110, in this example a patient in a bed 120, i.e. the person 110 being in a resting position. Said image data comprise a sequence of image frames over time. A device 2 according to the present invention is provided for automated detection of orientation and/or location of at least part of the person 110 based on the acquired image data. An output interface 3 is provided for issuing information related to the detected orientation and/or location of at least part of the person 110.

The imaging unit 1 may e.g. comprise one or more (for more robust detection and tracking) cameras. For instance, one or more video camera(s) mounted to the ceiling or wall of the room may be used. The imaging unit 1 e.g. captures the field of view in a patient room in a hospital, in particular the area of the patient bed 120.

The device 2 may substantially comprise or be implemented by a processing unit (e.g. a processor or computer) that receives the image information from the one or more cameras and analyzes them to detect the orientation and/or location of at least part of the person 110.

The output interface 3 is generally configured to issue information related to the detected orientation and/or location of at least part of the person 110, which may be configured in advance or which may be modified by the user. For instance, the output interface may be configured to issue audio-, visual- and/or text-based information. It may comprise a display 30 and/or a communication unit 31 that provides one or more kinds of alarms, e.g. to the clinical staff. The output interface 3 may thus e.g. be part of a portable user device, such as a smartphone, pager or body-worn device, such as a watch, or may be part of a stationary device, such as a computer, workstation or monitor at a nurse station. The display 30 may also be used to display one or more images acquired by the imaging unit 1 so that the user (e.g. the clinical staff) can judge the criticality of the situation. Also a summary of video actigraphy statistics (statistics about the movements of the person) in the last time, e.g. the last few hours, may be analyzed and displayed to support the user to judge the urgency or importance of the alarm and the detected event.

Figure 2:
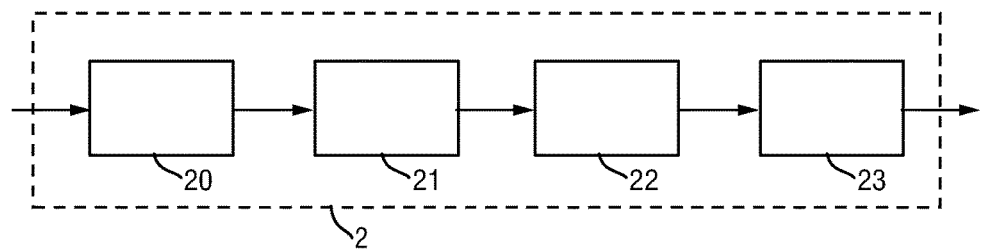
FIG. 2 shows a schematic diagram of a first embodiment of a device according to the present invention.

A schematic diagram of an embodiment of the device 2 is shown in FIG. 2. The device 2 particularly comprises an image data interface 20 for obtaining image data of a person 110, in particular from the imaging unit 1. A motion detector 21 is provided for detecting motion within said image data, e.g. by a conventional motion estimation or motion detection algorithm. A motion intensity detector 22 is provided for identifying motion hotspots representing image areas showing frequently occurring motion within a time period of several frames. Based on the identified motion hotspots a person detector 23 detects the orientation and/or location of at least part of the person 110.

Figure 3:
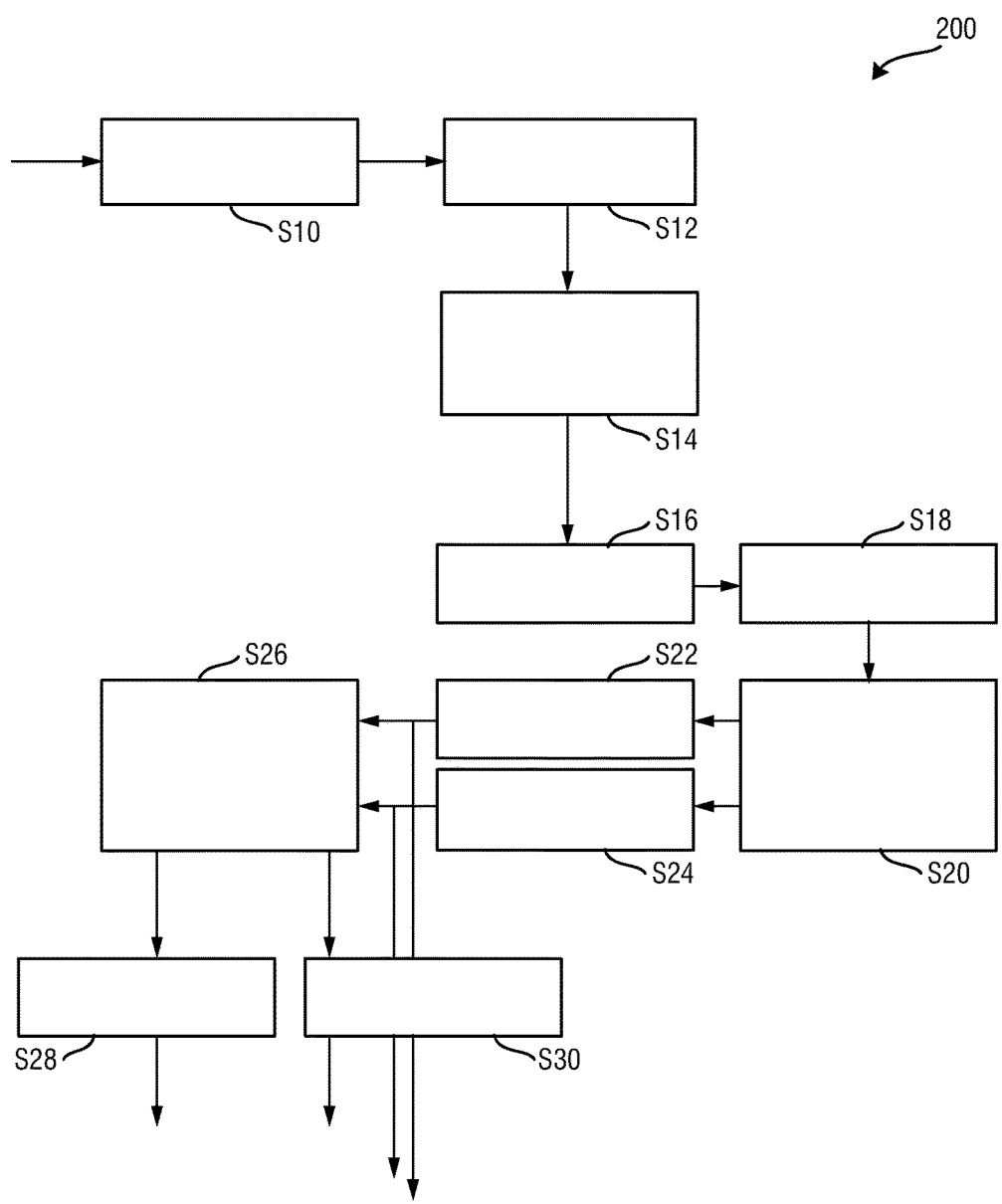
FIG. 3 shows a flow chart of a first embodiment of a method according to the present invention.

FIG. 3 shows a flow chart of a first embodiment of a method 200 according to the present invention. As exemplary embodiment a patient in a hospital bed shall be considered as e.g. shown in FIG. 1.

In a first step S10 motion estimation (or motion detection) is initially performed based on obtained image data, in particular a sequence of image frames obtained over time from the field of view of the imaging unit 1. Motion vectors are useful for obtaining information on the movement the patient 110 performs. Direction, speed, acceleration, and the size of the moving area are only a few parameters that can be deduced from motion vectors. This information helps greatly in recognizing patient movements and classifying them into natural and unusual movements (in which case the staff may be informed or warned).

Figure 4:
FIG. 4 shows an exemplary motion image obtain by motion detection.

An exemplary motion image 300 representing motion detected in image data is depicted in FIG. 4. An area 310 where a lot of motion of the patient 110 (in this example of the legs of the patient) has been identified is coded (e.g. with different colors, gray values, etc.) in said motion image 300 differently from other areas where no motion or less motion has been identified.

Figure 5:
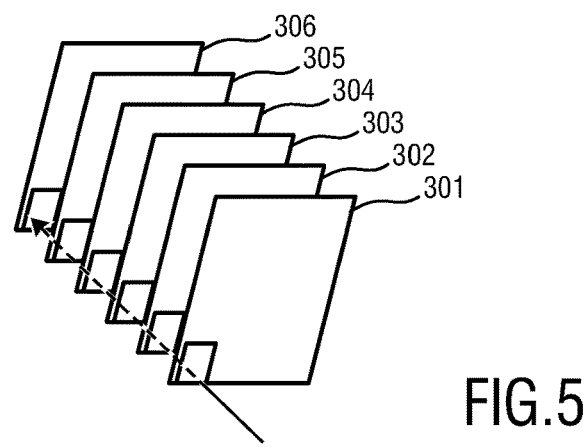
FIG. 5 shows a diagram schematically illustrating the accumulation of motion images.

In the next steps S12, S14 accumulated motion images (also called accumulation images herein) are computed. This may be achieved by summing up (step S14) the binary occurrences of motion pixels or motion vector information (e.g. the vector length) across an image stack, i.e. a number of motion images 301-306 covering a certain time period (as stacked in step S12). This is schematically illustrated in FIG. 5.

Exemplary output images (i.e. accumulation images) 400, 401, 402, 403 of accumulated motion images are shown in FIG. 6, in which areas H with high motion are coded in a first style (e.g. a first color or gray value) and areas L with low motion are coded in a second style (e.g. a second color or gray value) different from the first style.

Motion hotspots are computed in step S16, in particular by taking into account only large motion blobs and thresholding the accumulated motion images with an adaptive threshold (e.g. based on the motion strength in the image). If the patient is not sedated, most of the motion will come from the patient as the nurses/visitors are present only a small amount of time in the image. This can e.g. be seen in FIG. 6D where the motion hotspot H1 indicates most of the motion coming from head movements of the patient and hotspot H2 indicates movements of a nurse above the patient.

For the following explanation of an exemplary computation of patient boundaries in the images it shall be assumed that the image frames depict the patient somewhat from the side, i.e. the patient being depicted in a substantially horizontal direction. This is, however, not mandatory. The patient may e.g. also be depicted in vertical or inclined direction and the images may be rotated accordingly before further processing.

A temporary first (in this example upper) patient boundary is computed in step S18 from the accumulated motion images as the upper boundary of the detected motion hotspots. For instance, when passing through the image, this time from top to bottom, the image is analyzed per column. In an embodiment the pixel values per column are low-pass filtered, once strongly, once weakly. Then, the global maximum of the resulting strongly low-pass filtered signal is computed (likely to correspond to the patient, strongest hotspot). Next, minima are detected in the resulting weakly low-pass filtered signal (high peak corresponds to strong hotspot, like the nurse and part of the patient in FIG. 6D). Then, the minimum (computed in step S14) just before the maximum computed in step S12 is searched. Finally, the mean (across all columns) of the locations of the minimum computed in step S16 corresponds to the temporary upper patient boundary.

In subsequent step S20 the motion hotspots are added on to with smaller motion blobs (still large, but not as large as the initial motion blob requirement) with a centroid below the upper patient boundary. There are hotspots with different strengths. The strongest one belongs to the image area where the patient moved most. Around that one there are weaker hotspots also belonging to the patient. Some of these weaker hotspots may belong to body parts of the patient that extend outside the computed upper boundary. As long as the centroid of the hotspot is below the temporary upper boundary, it is assumed that it belongs to the patient.

Based on the newly formed upper boundary of detected motion hotspots, the final upper patient boundary is computed in step S22. The upper boundary of a weaker hotspot extending beyond the temporal upper patient boundary is selected as the final upper boundary. This final upper patient boundary 410 is e.g. shown in FIG. 6D.

A second (in this example lower) patient boundary 420 is computed in step S24 based on the bottom most hotspot H3. Several smaller motion hotspots are added (similarly as explained above) in step S26 between the upper and lower patient boundary 410, 420.

In order to compute the left and right boundaries 430, 440 of the patient ROI in step S28, the following steps are performed in an embodiment. For some or even each analyzed accumulated motion image the x coordinate of first samples (i.e., starting points) from left (or right) is stored when it exceeds k times the mean of the previous values (all samples from the left (or right) end up to the current sample). Clusters of similar starting points across the accumulated motion images are computed. The largest cluster indicates the left (or right) starting point. However, an edge strength as is computed above for indicating the left or right boundary can also be computed differently.

Figure 11:
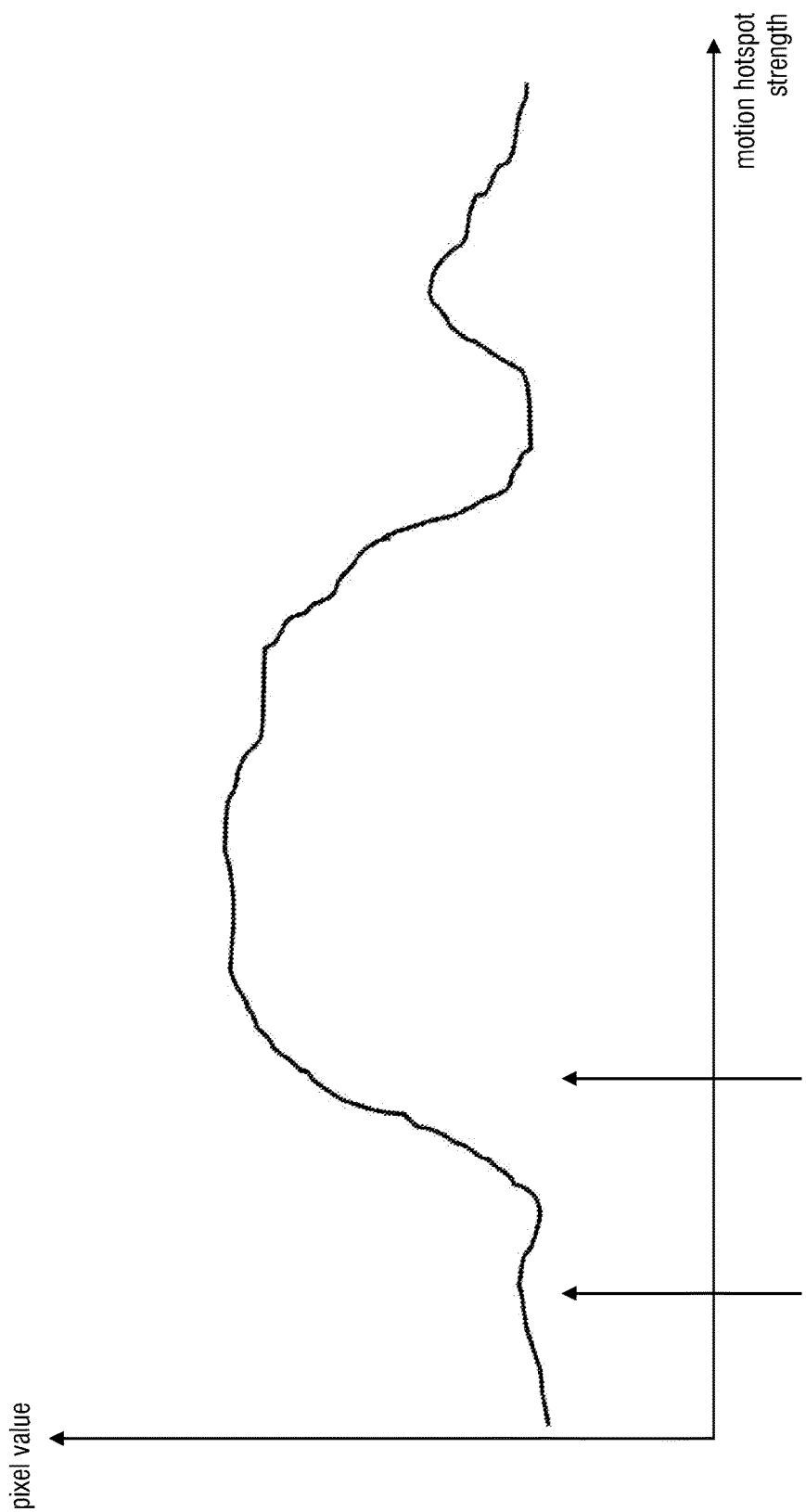
FIG. 11 shows a graph of pixel values over motion hotspot strength.

FIG. 11 shows a graph showing the pixel values (y-axis) corresponding to the motion hotspot strength for the entire row (x-axis) in an image. The first small maximum on the left corresponds to a nurse motion hotspot and the second higher maximum corresponds to the patient hotspot. In other words, the first arrow (from the left) indicates the area where a nurse was present from time to time. The second arrow indicates where the patient starts with a strong edge. The (in this example rectangular) patient ROI 450 enclosed by the boundaries 410, 420, 430, 440 is shown in FIG. 6D.

Still further, in step S30 a weighted average of nurse locations above the upper patient boundary 410 and below the lower patient boundary 420 is used to determine the location of the head (left or right in the image). For instance, the motion hotspot H2 above the patient ROI 450 indicates that there has been a lot of movement by a nurse/visitor. This increased movement is taken as a weight for the corresponding location in the weighted average computation. Due to the high presence of movements close to the head side of the patient (on the right side in FIG. 6D), the head location is estimated to be on the right of the ROI 450.

Furthermore, when the head location is known, the entire ROI 450 can be divided into coarse body parts like head, trunk, and legs according to average body proportions (e.g., the right most 15% are assigned to the head, the middle 35% are assigned to the trunk and the bottom 50% are assigned to the legs).

Figure 6A:
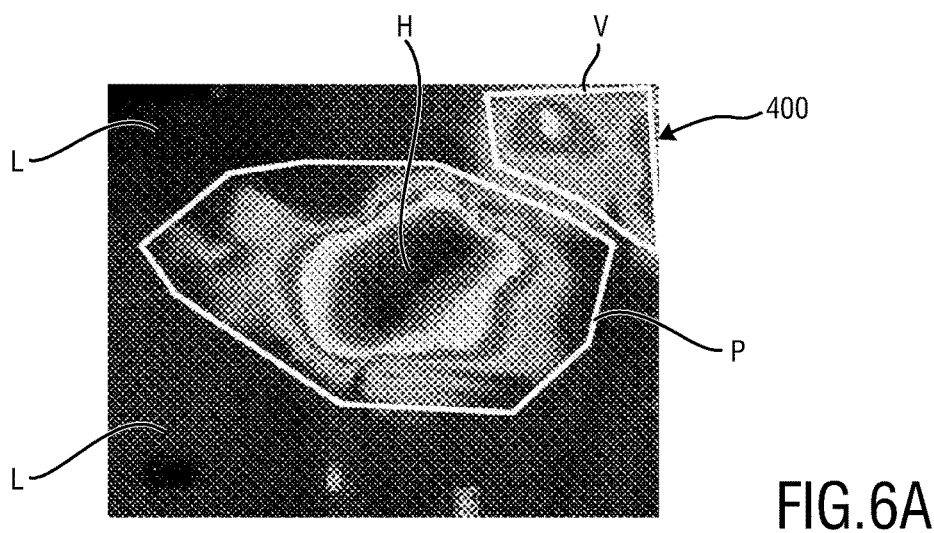
FIG. 6A, FIG. 6B, FIG. 6C and FIG. 6D show exemplary accumulation images obtained according to an embodiment of the present invention.
Figure 6B:
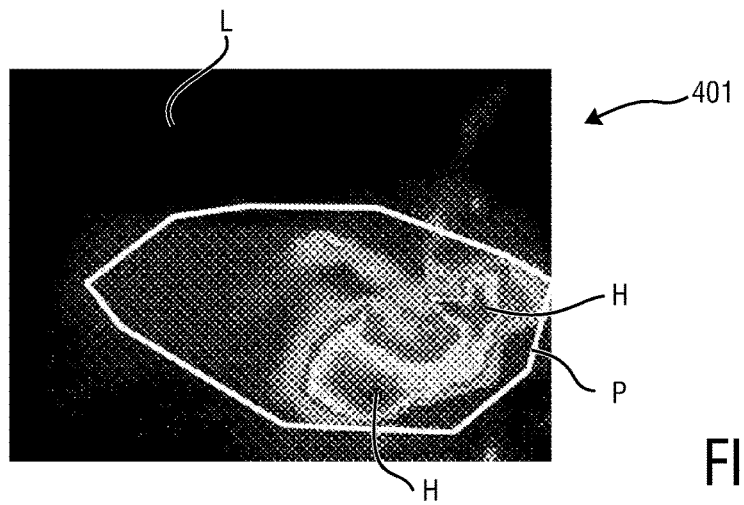
Figure 6C:
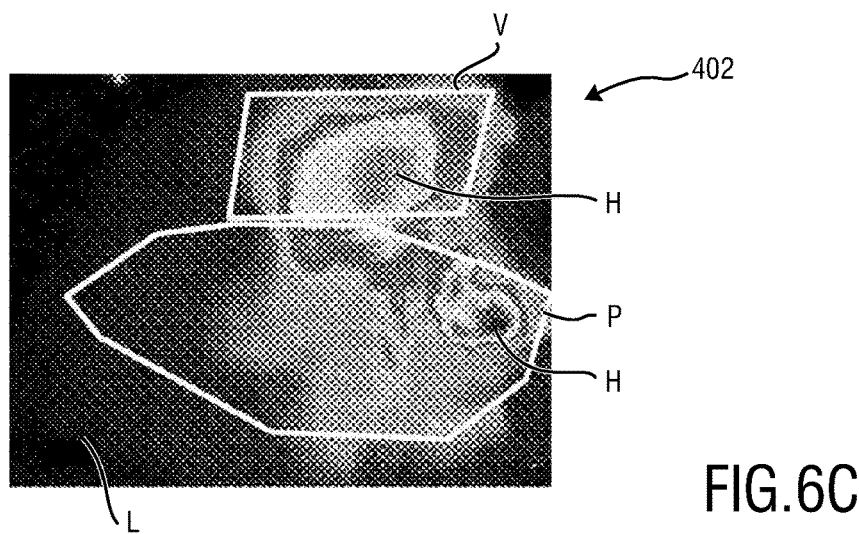
Figure 6D:
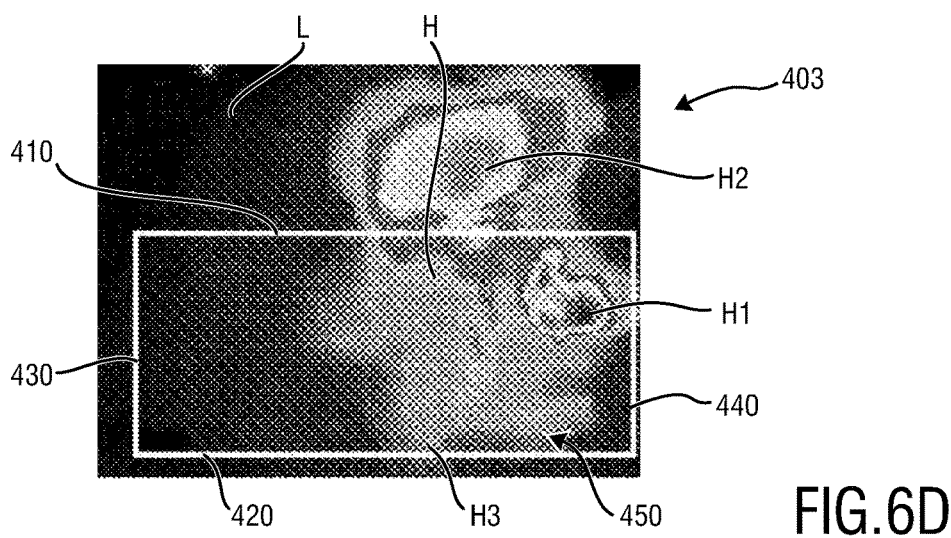

FIGS. 6A to 6C show further examples of accumulation images 400, 401, 402 in which the patient ROI has been estimated. FIG. 6A shows the result of an accumulation of motion pixels over 30 minutes. Visitors (and/or nurses) are present in the 30-minute video sequence, as indicated by the visitor/nurse area V; the patient, indicated by the patient area P, mainly moves his middle and lower body. FIG. 6B shows the result of an accumulation of motion pixels over 30 minutes, wherein the patient mainly moves his upper body. FIG. 6C shows the result of an accumulation of motion pixels over 30 minutes, wherein the patient mainly moves his head. A nurse has been moving/working/interacting close to the patient's upper body.

Figure 7:
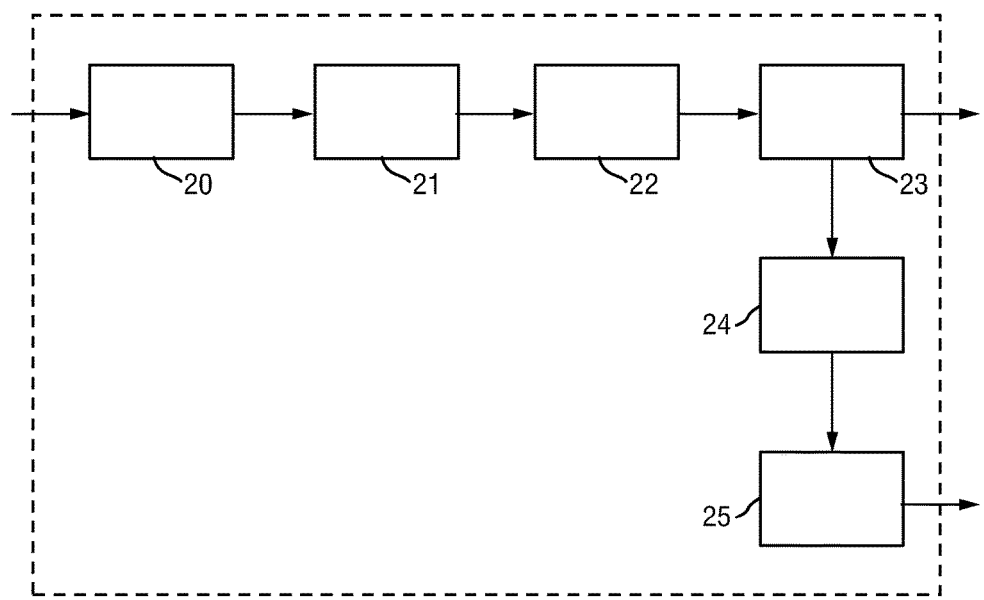
FIG. 7 shows a schematic diagram of a second embodiment of a device according to the present invention.

FIG. 7 shows a schematic diagram of a second embodiment of a device 2' according to the present invention. Besides the elements of the first embodiment of the device 2 shown in FIG. 2, it comprises an analysis unit 24 for analyzing movements of the person 110 or one or more body parts of the person 110 over time based on the detected orientation and/or location of at least part of the person 110 as detected regularly, continuously or from time to time, and an evaluation unit 25 for classifying the detected movements into natural and unusual movements, determining a disease severity score estimation and/or issuing an information signal in case the analyzed movements exceed predetermined criteria for issuing an information signal.

The analysis unit 24 particularly performs a patient whole body or body part activity analysis: The motoric information, for example, the mean activity value of patient's legs during night, is computed from motion estimation results. The data may be available continuously over 24 hours. The evaluation unit 25 particularly performs a movement classification. Disease-specific movements that could result in a dangerous situation for the patient or unusual movements (patterns) will be identified. Further, a disease severity score estimation may be performed, which will provide a score about the patient's condition to clinical staff by taking into account the outputs from the activity analysis and the movement classification.

In the hospital environment, there are several factors that may complicate the video analysis. For instance, the presence of visitors or clinical staffs in the room may obscure or overlap portions of the patient in the video image. In this case, segmentation of the movements from patient only is necessary. Therefore, more sophisticated elements need to be included in the system to solve all kinds of these practical issues. One example of a corresponding embodiment of the proposed method 300 is shown in the flowchart depicted in FIG. 8. In this embodiment, the processing can be regarded as two parallel tracks. One is to perform motion estimation, the other one is based on motion detection. However, there is no limitation to use motion estimation or detection, any method capable of detecting patient's motions can be utilized.

In step S100 motion detection is performed based on received image data. Due to practical issues in the hospital environment and/or video system, e.g., video compression artifacts or not optimal lighting conditions, the video quality might be not very good. Due to this the motion estimation could have difficulties in detecting small movements, for instance, patient's breathing motions. In this situation, it is proposed to use motion detection as a replacement.

There are several motion detection methods available. For instance, the frame differencing method detects the movement by e.g. calculating the sum of absolute differences (SAD) between two consecutive frames. Another widely used approach is correlation coefficient method. In the proposed device and method, there is no special requirement for particular method, but the choice might be dependent on the video quality, e.g., compression format.

Figure 8:
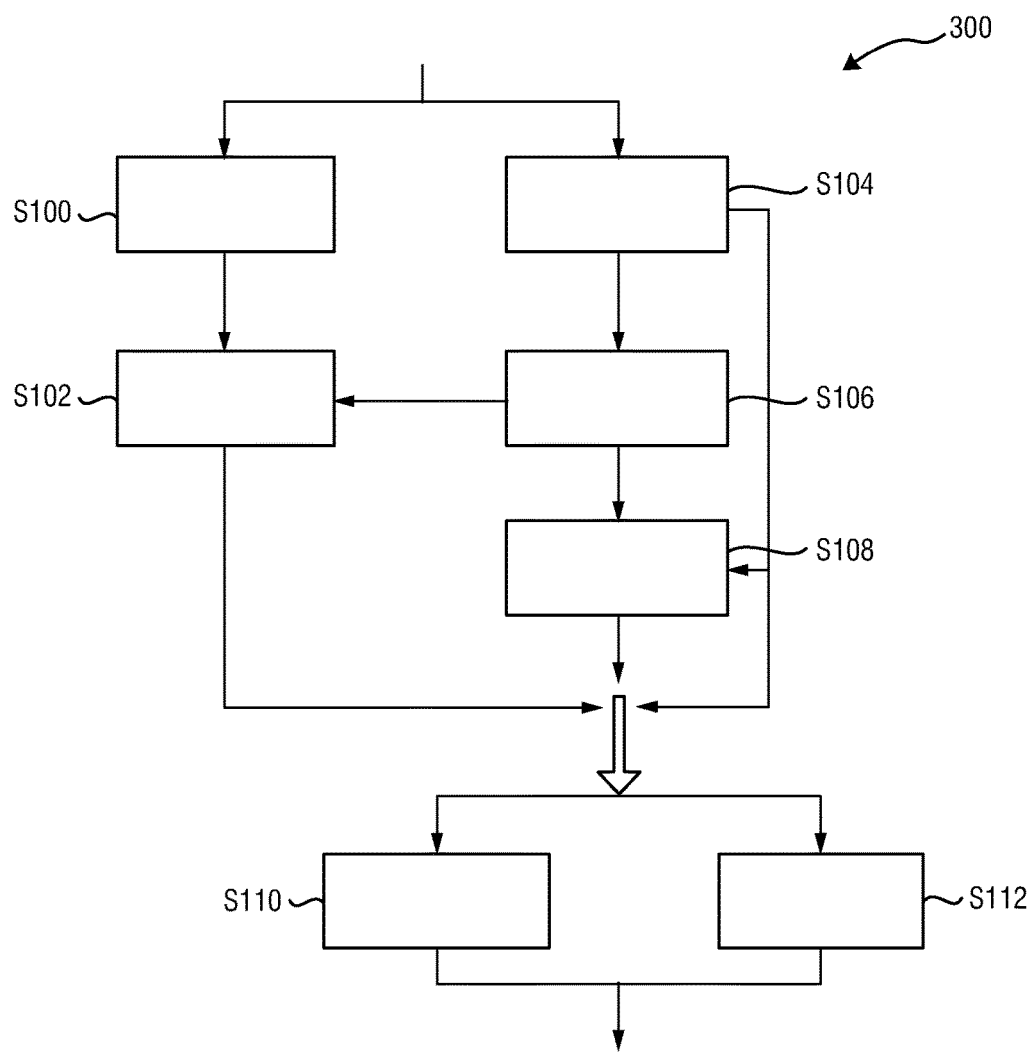
FIG. 8 shows a flow chart of a second embodiment of a method according to the present invention.

It can be seen in FIG. 8 that in step S102 performing body part segmentation the outputs from motion detection (step S100) used to detect patient's chest area are utilized, which will be described in more detail in the following.

In step S104 motion estimation is performed. Motion estimation (ME) is one option to capture the movements from a patient. The obtained motion vector field provides an indication of the motion location, strength and direction. In the proposed device and method, the ME algorithm based on the disclosure of A. Heinrich, C. Bartels, R. J. van der Vleuten, C. N. Cordes, G. de Haan, Optimization of hierarchical 3DRS motion estimators for picture rate conversion, IEEE Journal of Selected Topics in Signal Processing, vol. 5, no. 2, pp. 262-274, March 2011 as a solution, which can provide accurate motion vectors while maintaining a low computational complexity.

In step S106 patient body detection is performed and in step S108 nurse/visitor segmentation is performed. One dynamic aspect in hospital environment is the frequent presence of clinical staff and visitors in the patient room and thus in the video image. Because only the activities from the patient are of interests and need to be analyzed, other people's movements should be excluded. To differentiate their motions, it is proposed to perform patient body detection and nurse/visitor segmentation.

The step of patient body detection S106 is used to search for the region of interest (ROI), i.e., the patient body area. This can be done as explained above with respect to the first embodiment of the device and method according to the present invention. The main idea is to accumulate motion vectors obtained from motion estimation module over a period of time. As people other than the patient might also be present in the video, the selected accumulation time should be long enough so that the dominant motions are from patient. An example of accumulated vectors is shown in FIG. 6D which is obtained from a video of 30 minutes in which the patient is mainly moving his middle and lower body parts, and also a nurse is present in the sequence (represented by the hotspot H2). By increasing the accumulation time and performing some post-processing, the motion vectors from the nurse may even be eliminated.

When the patient body area has been determined, it is then possible to segment the nurse/visitor out. The proposed method is to keep motion history information and to differentiate the motions from different people by tracing their origins. By doing this, the motion history image can be separated into patient history image and nurse/other people history image. Other methods could also be applied here as well to detect the image area of the nurse/visitor.

In step S102 body part segmentation is performed, which may be done as explained above with respect to the first embodiment. The body part segmentation step is used to identify different body parts of the patient. Patient's body parts, such as head, trunk and legs, can be differentiated from each other. As a result motion analysis can be performed per body part, which provides more detailed motion information of the patient's motoric behavior. Further, based on the identification of the different body parts the location and orientation of the respective body parts as well as the location and orientation of the whole patient can be determined.

For instance, if the movements from patient's legs are of interest, clinical staff can have a look at the mean activity level of this body part over the past 24 hours. Besides this activity analysis, the movement classification will also benefit a lot from this segmentation information. It is much easier to identify certain movement patterns performed by a specific body part if the body part location is already known.

Figure 9A:
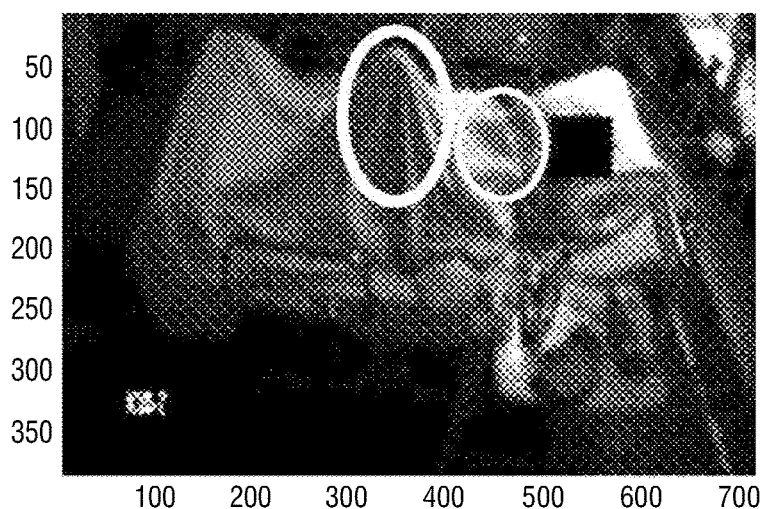
FIG. 9A and FIG. 9B show an acquired image frame and a corresponding accumulation image.
Figure 9B:
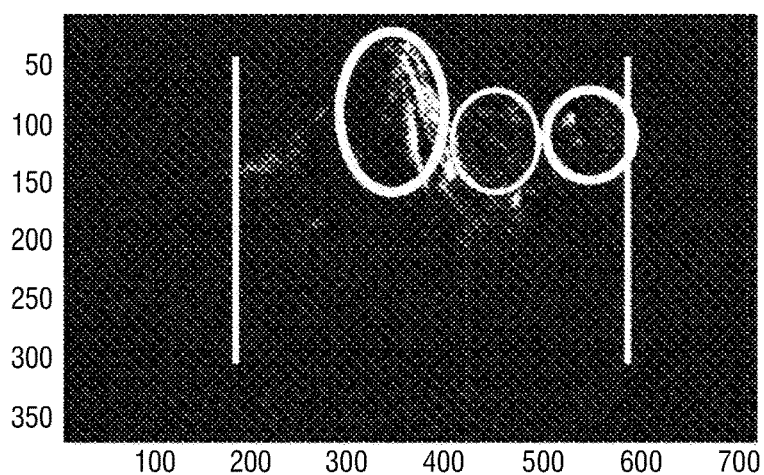

Different approaches to segment body parts can be applied. A simple method could be to split the whole body area into several parts by ratio numbers. For example, the ratios for the head, truck and legs are set to 15%, 30%, 55% respectively. Further, a more sophisticated method may be used which is based on chest detection. The idea is to determine chest area first by detecting breathing motions, the remaining head and legs parts are then split afterwards. This is depicted in FIG. 9, wherein FIG. 9A shows an acquired image in which several body parts are highlighted and FIG. 9B shows a corresponding accumulation image in which the movements of the same body parts are highlighted.

Figure 10A:
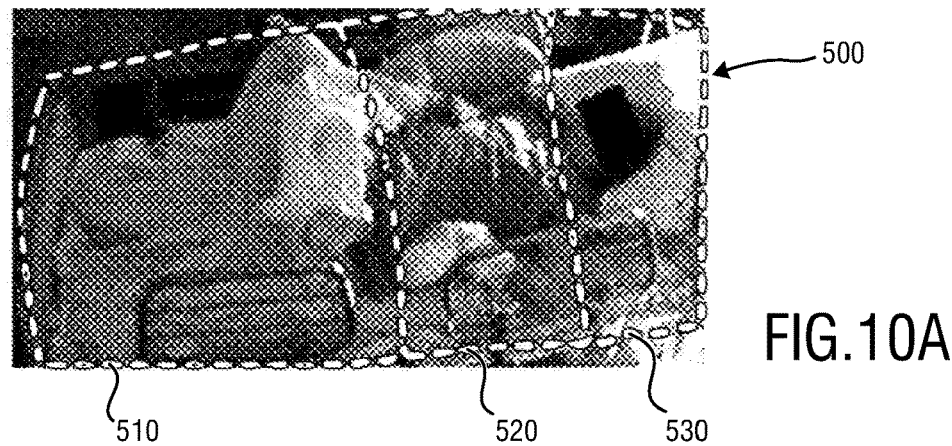
FIG. 10A and FIG. 10B show an acquired image frame and various graphs comparing measurements from a body-mounted activity sensor to measurements obtained from image data.
Figure 10B:
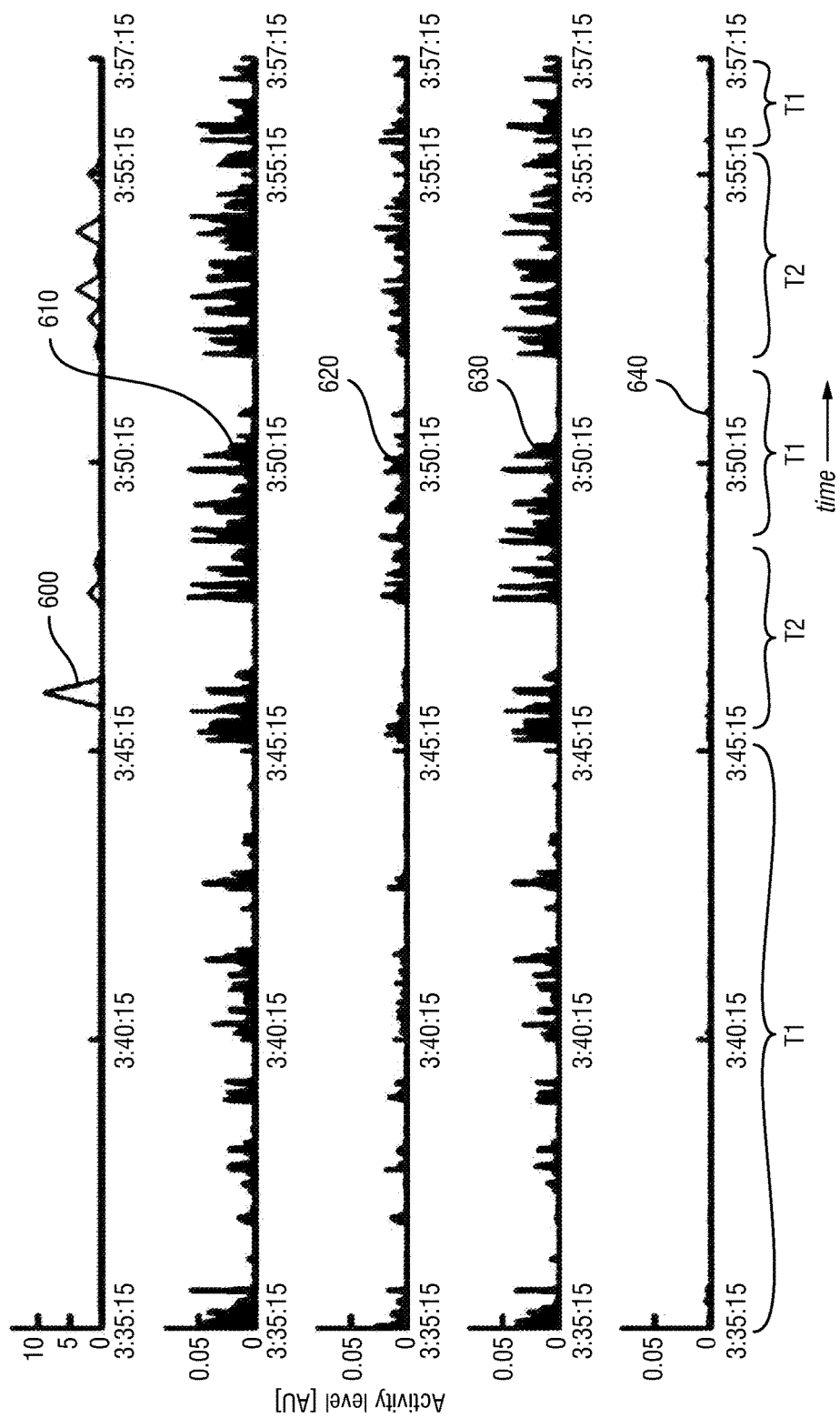

In step S110 activity analysis is performed. Body part/whole body activity level analysis is besides movement classification one of the two elements to analyze patient's movements. It provides an overview of patient activities and can be used as one criterion to determine the clinical condition of the patient. FIG. 10A shows an example of an image 500 of a patient in which the three areas legs 510, trunk 520 and head 530, as derived by body part segmentation, are indicated. FIG. 10B shows different activity level signals, wherein the activity level signal 600 is obtained from an activity monitoring device, such as wrist worn device (e.g. the applicant's device called "Actiwatch"), compared to activity level signals obtained by video actigraphy of the total body (signal 610), the trunk (620), the legs (630), and head (640).

The advantage is clearly observed in the time periods indicated by T1 in FIG. 10B: motions from e.g. the legs and head, where no signal (see signal 600) from the activity monitoring device is available, e.g. because the sensor is not worn by the patient, signals can still be detected by video. By visual inspection of the video and the video actigraphy signal(s) it was shown that also movements of the other arm, on which no activity monitoring device is worn, were detected correctly which are reflected in the trunk activity signal 620. The time periods T2 show that the video system is very well able to detect movement also measured with the activity monitoring device.

Different activity statistics may be computed here, for instance, mean or variations of activity value for one particular body part in selected time period, frequency of activity, etc. This information can be used to distinguish if changes in motoric alterations are occurring which could be indicative for certain clinical conditions such as delirium, epilepsy, or Parkinson, restless legs. In addition, this motoric analysis will also contribute to movement classification, because these activity levels can be utilized as classification feature.

In step S112 movement classification is performed. Compared to body activity analysis, motion classification provides a higher level interpretation of patient's movements. It can differentiate between natural and unusual movements and can further identify specific movement (patterns). For example, in the case of delirium, movements such as grabbing in the air or picking the skin are typical movements. Detection of these specific motions will directly contribute to patient delirium assessment. In other applications tremors indicative for Parkinson or epileptic seizures may be detected. There are also other benefits obtained from this movement recognition. It can be also used to detect some movements that can result in dangerous situations. For example, if patient is trying to get or is falling out of the bed, pulling out for example the endotracheal tube or feeding tube, etc. This embodiment of the proposed method and device can the automatically send a warning message to medical staffs.

As to the classification method, any type of classifiers suitable for this problem can be used. Motion features, such as motion direction, speed, acceleration, and the size of the moving area, can be deduced directly from motion vectors. Other feature examples include movement duration and frequency/repetitiveness. Considering particular movements are normally performed by specific body parts, the classifier will profit from body part information. It is therefore proposed in an embodiment to extract motion features per body part.

Further, disease severity score estimation may be performed. This step provides a score on the severity of the disease. It estimates the patient's health condition by combining the data of video analysis. In the proposed embodiment of the device shown in FIG. 7, the output is based on video actigraphy and movement classification (i.e., detection of specific movements related to the clinical condition if interest). However, it is not limited to video, other complementary information, if available, can all be fed into this step and can be taken into consideration for a final decision. This could be data measured with other sensor modalities, clinical tests/screenings or observations of clinical staff.

An alarm may be given when changes in the clinical conditions are detected which is indicative for the clinical condition of interest, or when movements are detected which could be of danger for the patient such as trying to get out of bed. When the score passes a pre-set threshold the medical staffs may automatically receive a warning message. Clinical staff can set the alarms they are interested in and which diseases/disorder should be detected or has highest priority.

The elements and steps explained above are not limited as described above. More sophisticated elements and steps may be added, and other combinations may be made, to get a better performance.

Because people other than the patients are often present in the video, the movements of the patient sometimes cannot be captured by the camera due to obstruction. If it is not possible to install the camera such that only the patient is in view (e.g. above the patient), a second camera may be installed in the room to image the patient from a different view direction. In this case, extra video processing, such as camera synchronization and camera selection, might be required to get a better view condition.

In another embodiment, prior knowledge on the patient location and patient orientation in the image may be used by acquiring input from the hospital staff when a measurement begins or when a situation has largely changed.

The bed position or bed angle can be changed as result the patient position is changed and also the body part segmentation. The patient body detection module should then be updated. As an additional embodiment automatic bed detection could be implemented to signal change in bed position or bed angle.

In summary, the invention is applicable in various areas, particularly for patient monitoring in hospitals at different wards in the hospital (e.g. ICU, acute care settings, general wards, geriatric wards) or care centers, nursing homes, NICU, at home where automatic and continuous video movement analysis is performed. Main fields of application are early detection of delirium or other diseases with unusual movements/behaviors, e.g. related to delirium, where automatic video monitoring in the ICU is applied, and (healthy or unhealthy) elderly monitoring to trigger alerts to the caregivers at home, in nursing homes, or in elderly care centers.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for automated detection of orientation and/or location of a person, comprising:
   an image data interface configured to obtain image data of a person, said image data comprising a sequence of image frames over time,
   a motion detector configured to detect motion within said image data,
   a motion intensity detector configured to identify motion hotspots, wherein the motion hotspots show areas of the image frames with frequently occurring motion,
   a person detector configured to identify the motion hotspot showing the most intensive motions over a predetermined time period as a first boundary of the person.

2. The device as claimed in claim 1, wherein said motion detector is further configured to determine motion images representing motion detected within said image data from one image frame to another image frame and wherein said motion intensity detector is configured to identify motion hotspots by accumulating said motion images.

3. The device as claimed in claim 2, wherein said person detector is further configured to detect a left and/or right boundary of the person in an image by edge strength analysis in one or more accumulated images in a direction substantially parallel to the longitudinal axis of the person.

4. The device as claimed in claim 3, wherein said person detector is further configured to cluster edges detected in several accumulated images and to identify the largest cluster of edges to the left and right, respectively, as the respective boundary.

5. The device as claimed in claim 1, wherein the first boundary is an upper boundary of the person in an image.

6. The device as claimed in claim 1, wherein said person detector is further configured to identify the motion hotspot located farthest away from the first boundary towards an edge of the image opposite the first boundary as a second boundary of the person in an image, wherein the first boundary is an upper boundary and the second boundary is a lower boundary.

7. The device as claimed in claim 6, wherein said person detector is further configured to identify locations of body parts of the person based on the detected upper and/or lower boundary and known or average body proportions of the person.

8. The device as claimed in claim 1, wherein said person detector is further configured to detect the presence, orientation and/or location of one or more additional persons or at least parts thereof based on the identified motion hotspots and to use the result of this detection in the detection of the orientation and/or location of at least part of the person.

9. The device as claimed in claim 8, wherein said person detector is further configured to use the intensity, location, pattern and/or duration of motion of said one or more additional persons in the detection of the presence, orientation and/or location of one or more additional persons or at least parts thereof and/or in the orientation and/or location of at least part of the person.

10. The device as claimed in claim 1, further comprising:
an analysis unit configured to analyze movements of the person or one or more body parts of the person over time based on the detected orientation and/or location of at least part of the person as detected regularly, continuously or from time to time, and
an evaluation unit configured to classify the detected movements into natural and unusual movements, determining a disease severity score estimation and/or issuing an information signal in case the analyzed movements exceed predetermined criteria for issuing an information signal.

11. A device for automated detection of orientation and/or location of a person, comprising:
an image data interface configured to obtain image data of a person, said image data comprising a sequence of image frames over time and to determine motion images representing motion detected within said image data from one image frame to another image frame
a motion detector configured to detect motion within said image data,
a motion intensity detector configured to identify motion hotspots which show areas of the image frames with frequency occurring motion and to accumulate motion images covering a predetermined time period, to obtain one or more accumulation images by summing up binary occurrences of motion pixels or motion vector information within two or more motion images,
a person detector configured to detect an orientation and/or location of at least part of the person based on the identified motion hotspots.

12. The device as claimed in claim 11, wherein said motion intensity detector is further configured to identify image areas as motion hotspots, which have a size above a size threshold or the largest sizes within one or more accumulation images and which show motion above a motion threshold or the most intensive motions.

13. A system for automated detection of orientation and/or location of a person, comprising:
one or more video cameras configured to acquire image data of a person, said image data comprising a sequence of image frames over time;
the device as claimed in claim 1 for automated detection of orientation and/or location of at least part of the person based on the acquired image data, and
an output interface configured to output information related to the detected orientation and/or location of at least part of the person.

14. A method for automated detection of orientation and/or location of a person, comprising:
obtaining image data of a person, said image data comprising a motion estimation in a sequence of accumulated image frames over time,
detecting motion within said accumulated image data,
determining motion images representing motion from one image frame to another image frame in the accumulated image data,
identifying motion hotspots representing image areas showing most intense motion over a predetermined period of time, taking into account large motion areas and thresholding the accumulated image data with an adaptive threshold,
identifying a boundary of the person based on the identified most intense motion hotspots.

15. A non-transitory computer readable medium with a computer program with executable instructions causing a computer to carry out the steps of the method as claimed in claim 14 when said computer program is carried out on the computer.

16. A device for automated detection of orientation and/or location of a person, comprising:
one or more video cameras configured to generate image data of a person including a sequence of video frames of the person;
one or more computer processors programmed to:
receive the image data from the one or more video cameras;
detect motion within the image data from the one or more video cameras;
identify motion hotspots within the image data from the one or more video cameras by accumulating image data over a plurality of rames, wherein the motion hotspots show areas with frequently occurring motion;
detect a left and/or right boundary of the person in an image by edge strength analysis in one or more accumulated images in a direction substantially parallel to the longitudinal axis of the person based on the identified motion hotspots; and
a user interface configured to output information related to the detected left and/or right boundary of the person.

* * * * *